United States Patent [19]

Madis et al.

[11] Patent Number: 4,861,761
[45] Date of Patent: Aug. 29, 1989

[54] ALOEFERON ISOLATION, MANUFACTURING AND ITS APPLICATIONS

[75] Inventors: Valdemar H. Madis; Mostafa M. Omar, both of Hawthorne; Voldemar Madis, Ho Ho Kus, all of N.J.

[73] Assignee: Dr. Madis Laboratories, Inc., S. Hackensack, N.J.

[21] Appl. No.: 833,084

[22] Filed: Feb. 24, 1986

Related U.S. Application Data

[63] Continuation of Ser. No. 625,521, Jun. 28, 1984, abandoned.

[51] Int. Cl.$^4$ ............................................. A61K 31/715
[52] U.S. Cl. ..................................... 514/54; 514/844; 514/859; 514/861; 514/864
[58] Field of Search ............... 424/195.1; 514/54, 844, 514/859, 861, 864

[56] References Cited

U.S. PATENT DOCUMENTS

| | | | |
|---|---|---|---|
| 3,103,466 | 9/1963 | Farkas | 514/54 |
| 3,362,951 | 1/1968 | Farkas et al. | 536/121 |
| 3,892,853 | 7/1975 | Cobble | 424/195.1 |
| 4,225,486 | 9/1980 | Suzuki | 530/378 |
| 4,488,482 | 12/1984 | Cottrell | 100/37 |
| 4,598,069 | 7/1986 | Hikino et al. | 514/54 |

OTHER PUBLICATIONS

Mandal et al., Carbohydrate Res. 87:249–256, 1980.
Mandal et al., Ind. J. Chem. 22B:898–893, 1983.
Chem. Abst. 86:86163r, 1977.
Chem. Abst. 94:136159g, 1981.

Primary Examiner—John W. Rollins
Attorney, Agent, or Firm—Kenyon & Kenyon

[57] ABSTRACT

The present invention is directed to a substantially pure therapeutically active aloe isolate having a molecular weight of about 70,000 and a dialysis method for making said aloe isolate.

5 Claims, 4 Drawing Sheets

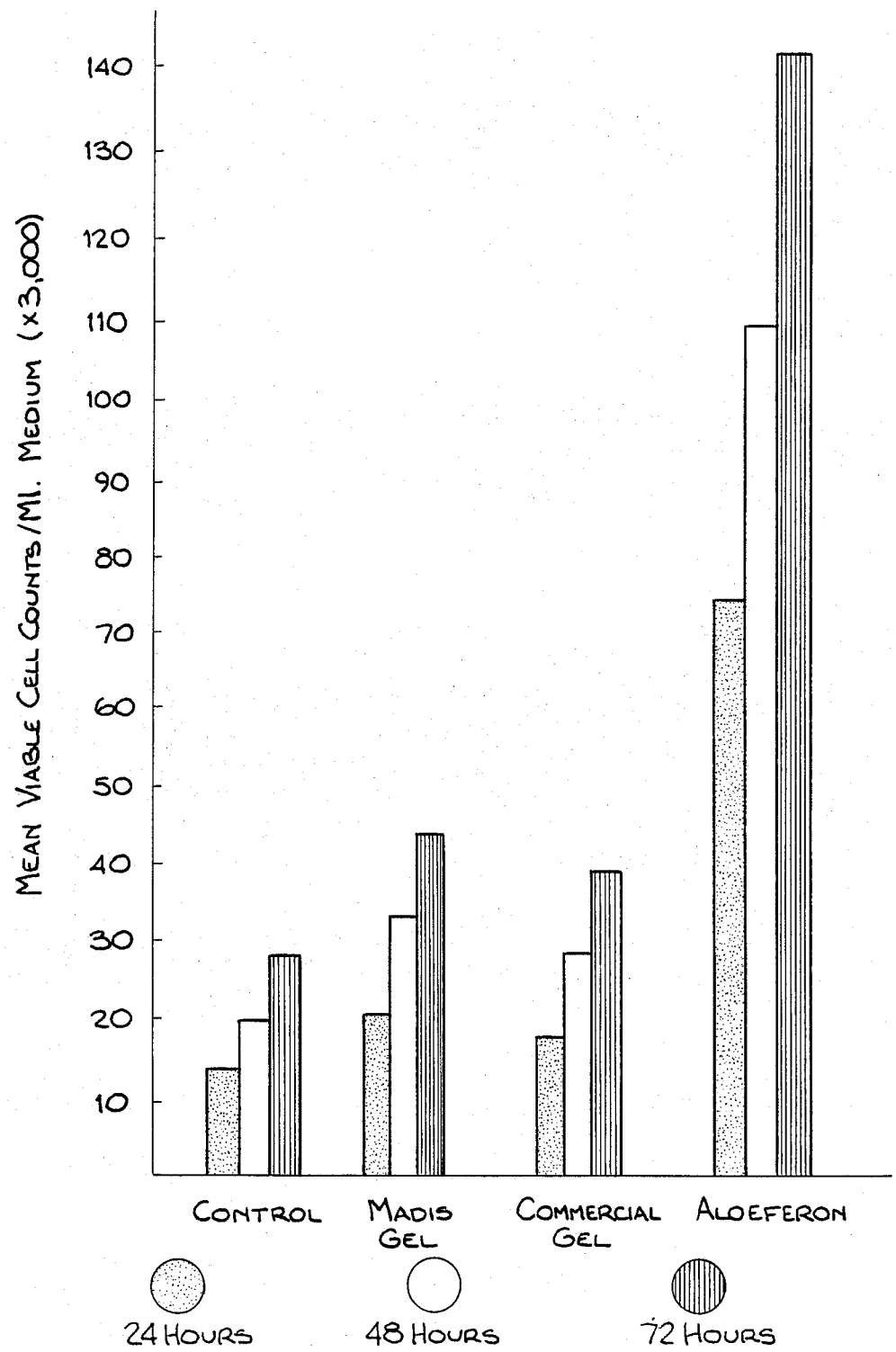

ALOEFERON ISOLATION, MANUFACTURING AND ITS APPLICATIONS

CROSS-REFERENCE TO RELATED APPLICATION

This application is a continuation of U.S. Ser. No. 625,521 filed June 28, 1984, now abandoned.

FIELD OF THE INVENTION

The present invention relates to a therapeutically active substance isolated from aloe plants and methods for the preparation and use thereof.

BACKGROUND OF THE INVENTION

It has long been known that products of the aloe plant, particularly, *aloe vera L.* (*aloe barbadensis* Miller) are useful as medicaments in the treatment and healing of a wide variety medical disorders. From ancient times, to the present, aloe gel has been reported to be useful in the treatment of medical disorders in almost every field of medicine from psychiatry to oncology, e.g., insomnia, insect bites and stings, infections, herpes, rheumatism, etc., and aloe is known to be particularly effective in treating skin-related disorders.

Many attempts to identify and isolate therapeutically active components from aloe plants have been made in the prior art. For example, U.S. Pat. No. 3,103,466 is directed to medicaments useful for treating surface wounds that include a polyuronide isolated from aloe gel which comprises a polysaccharide having chemically bonded thereto one or more hexuronic acid radicals having a molecular weight from about 374,000 to 275,000 or the non-toxic salts thereof.

U.S. Pat. No. 3,362,951 is directed to a therapeutically active polysaccharide derived from the juice of aloe plants by mixing the juice with a dilute aqueous solution of phosphomolybdic acid; separating the resulting precipitate from the aqueous solution; mixing a lower aliphatic polar solvent with the aqueous solution; separating the resulting blue-green precipitate therefrom and adding aqueous hypochlorous acid until the precipitate turns essentially white and recovering the white precipitate which when washed with a water soluble polar solvent is a highly pure polysaccharide in the form of long polymer chains (molecular weight about 420,000 to 520,000) comprised of repeating units containing substantially equal amounts of glucose and mannose residues, a small proportion of glucuronic acid residue and chemically bound calcium.

U.S. Pat. No. 4,225,486 is directed to a medicinally useful glycoprotein isolated from aloe plants and having a molecular weight of about 18,000, a protein to sugar ratio of 8 to 2 by weight and other specified properties. The glycoprotein is prepared by precipitating a fraction from aloe juice with ammonium sulfate; dialyzing the precipitate to remove the ammonium sulfate; acidifying the dialyzed solution and collecting the precipitate; dissolving the precipitate in buffer and separating the protein product on a Sephadex G-200 column.

OBJECTS OF THE INVENTION

It is an object of the present invention to provide an economical one-step method for isolating from aloe plants a substantially pure therapeutically active polysaccharide linked with nitrogen, sulfur and phosphorous and having a molecular weight of about 70,000; that does not involve the use of organic solvents, heat, chromatography or ion exchange, absorption or elution methods and that eliminates harmful components, e.g., oxalic acid.

It is another object of the present invention to provide an aloe isolate which has useful thereapeutic properties including the acceleration growth, multiplication and healing of cells.

It is another object of the present invention to provide a polymer polysaccharide having bactericidal properties that can be stored without the aid of preservatives and stabilizers.

It is another object of this invention to provide substantially pure aloe isolate that includes the primary biologically active ingredient of aloe gel and that has value in the treatment of gastrointestinal disorders, tumors, various skin ailments and as an antidote for certain poisons.

It is yet another object of the present invention to provide a substantially pure aloe isolate suitable for use as an additive to cosmetics, pharmaceuticals, soaps, detergents and the like to ameliorate the effects of cell damage.

It is also an object of this invention to provide an assay for the potency and strength of aloe gels that conforms with the FDA requirements for use of said gels in food, drug and cosmetic products.

SUMMARY OF THE INVENTION

The present invention provides a non-destructive method for preparing an aloe isolate comprising the steps of separating a gel from an aloe plant and dialyzing the separated gel against water until the non-dialyzable fraction has a molecular weight of about 70,000; and collecting the non-dialyzable fraction which is the aloe isolate of this invention. This method is non-destructive because it does not employ conditions or chemicals, such as acids and organic solvents, which cause changes in the molecular structure of the natural aloe isolate.

The aloe isolate of the present invention, which may be prepared by the foregoing method, comprises a polysaccharide linked with nitrogen, sulfur and phosphorous and having the following elemental analysis:

| C | about | 38.60% | S | " | 1.04% |
|---|---|---|---|---|---|
| H | " | 6.20% | N | " | 0.13% |
| O | " | 53.80% | P | " | 0.13%. |

BRIEF DESCRIPTION OF THE DRAWINGS

FIG. 3, is a NMR spectrogram of the aloe isolate of the present invention; and

FIG. 4, is a bar graph illustrating the effectiveness of the aloe isolate of the present invention in enhancing cell growth compared to commercially available aloe vera gels.

DETAILED DESCRIPTION OF THE INVENTION

The aloe isolate of the present invention may be prepared from the whole aloe plant, or parts thereof, e.g. whole leaf or gel extracted from mucilagineous parenchyma (inner or central zone) by squeezing, pressing, filleting or other extraction methods suitable for removing lignin walled cells, connective tissues, fibers, lignified sturdy veins, and clusters of calcium oxalate raphides sand and substances responsible for rapid discoloration and accelerated decomposition of the gel. The preferred aloe plants for purposes of this invention are *aloe vera linne* (*aloe barbadensis* Miller) Fam. Liliaceae or any of the 500 or so species of aloe containing the polysaccharide of this invention. The gel has a firm consistency only in the fresh aloe leaf. During processing and purification of the aloe leaves the thin walled cells are disrupted and removed and the gel contained within becomes watery and slightly colloidal. Any contamination with yellow juice ingredients (anthraquinones) must be avoided because such compounds may produce allergic reactions and are considered contaminants.

Figure 1:
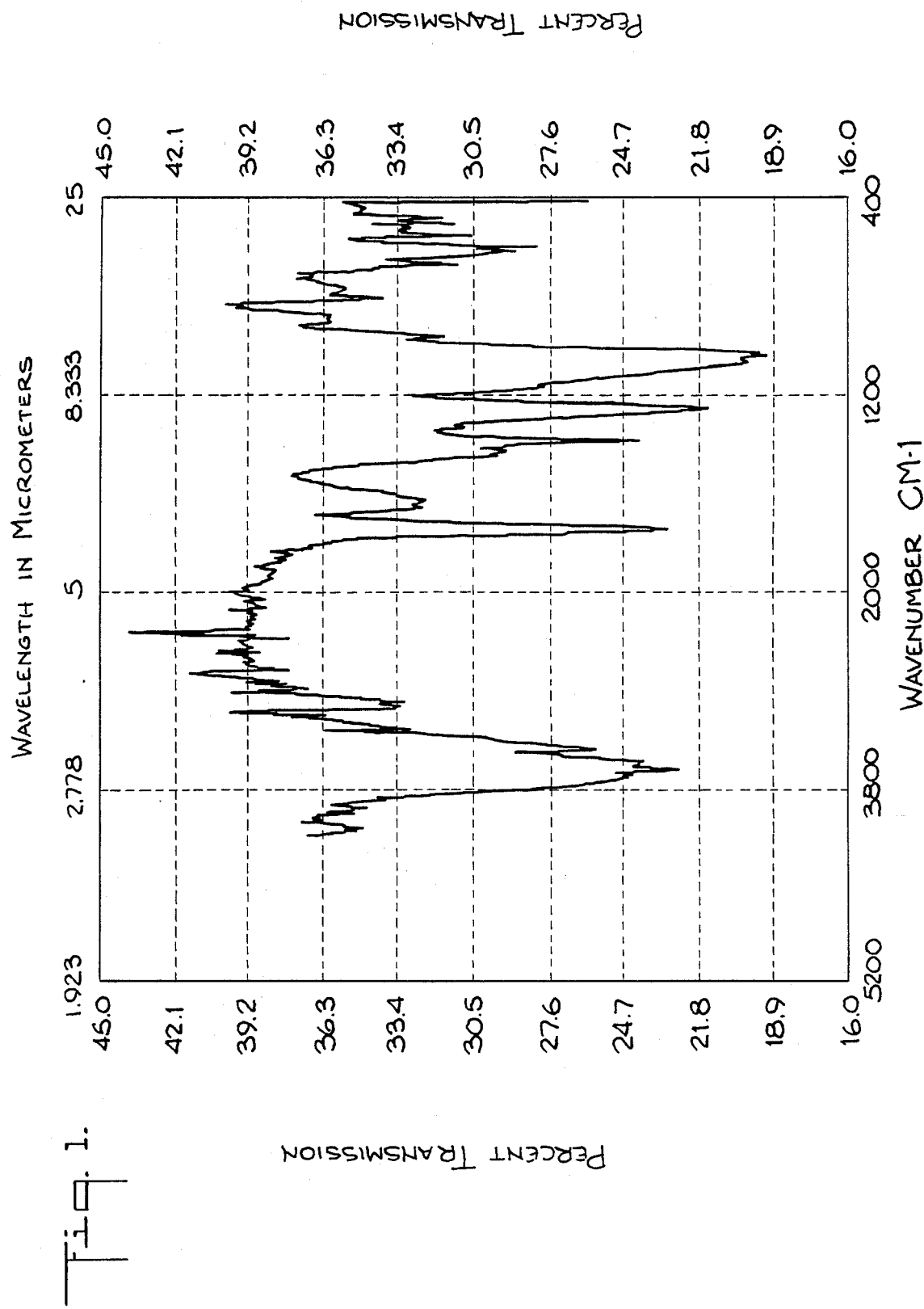
FIG. 1, is an infra-red spectrogram of the aloe isolate of the present invention.

The aloe isolate of this invention may be identified by its infra red spectra which is characterized by strong absorbance peaks at 3400 and 1720 cm$^{-1}$ and medium absorbance peaks at 2900, 1550 and 1420 cm$^{-1}$ as shown in FIG. 1.

Figure 2:
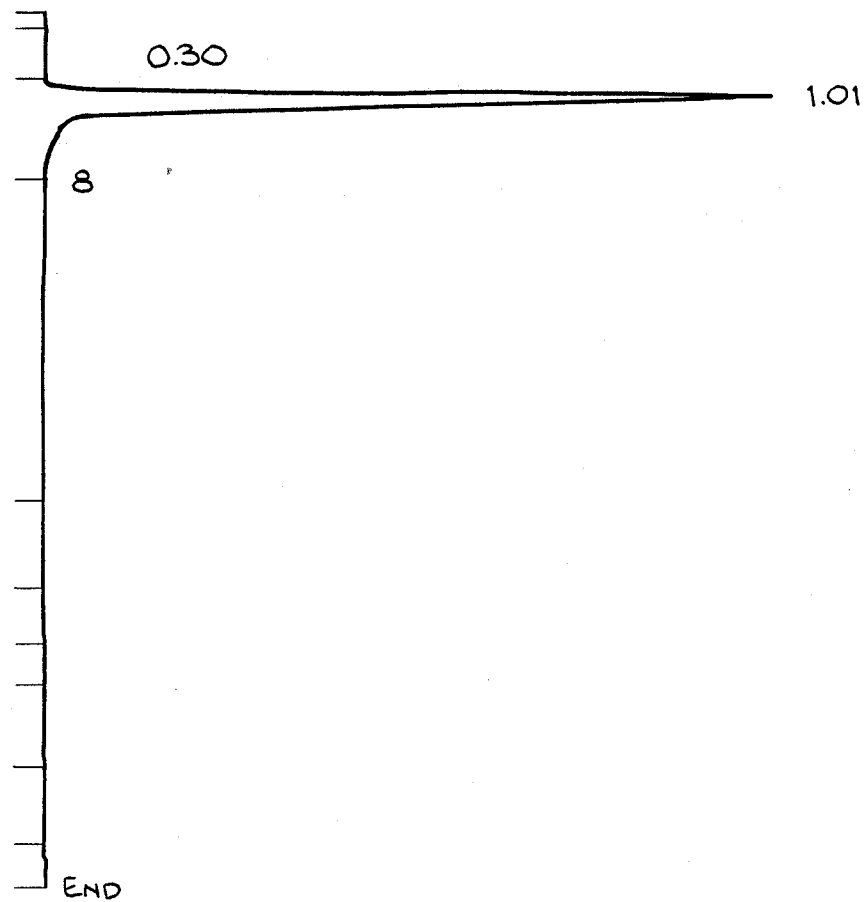
FIG. 2, is a HPLC chromatogram of the aloe isolate of the present invention.
Figure 8:
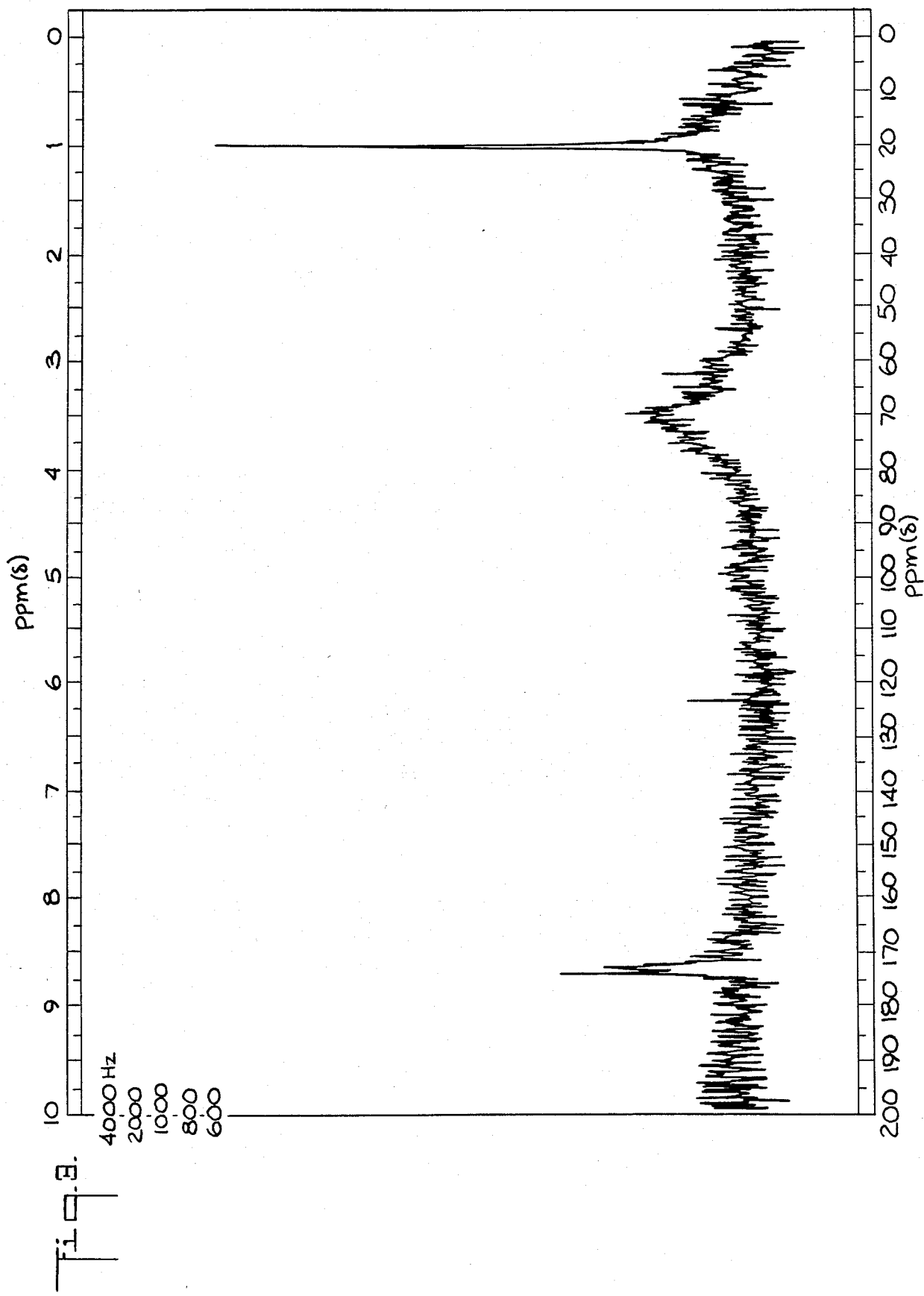

A preferred method for quantitative analysis of the aloe isolate of this invention is high pressure liquid chromatography (HPLC) employing a $C_{18}$ column, an acetonitrile-water mobile phase and photometric detection at 200 nm. This method produced the single peak chromatogram of FIG. 2 and the concentration of aloe isolate in a sample can be calculated from the area under the peak. This HPLC method may be effectively used for determining the potency and purity of aloe gel and aloe isolate products in accordance with FDA requirements.

The aloe isolate of this invention has the NMR spectra shown in FIG. 3 which may be characterized as follows:

| Chemical Shift | Spectral Pattern | Chemical Group |
| --- | --- | --- |
| 20 ppm | sharp single | methyl |
| 70 ppm | broad multiple | sugar residue |
| 174 ppm | broad multiple | acetate |

Aloe Vera L. plants each having an average weight of about 5 Kg. were processed in accordance with the invention to prepare the desired aloe isolate. Before the extraction of the gel was begun, latex (red juice) was drained off by cutting their leaves near the basal end and bleeding them. The leaves were then cut parallel to their base and the jelly like layer was removed by filleting. Plants of about 5 kg produced about 2 kg of gel and single average leaves of about 400 grams produced about 180 grams of gel. The separated gel was blended in a high speed mixer and filtered through gauze twice and then through coarse filter paper under vacuum. The resulting cloudy, milky filtrate was dialyzed against distilled water for about fifteen (15) hours in an ultrafiltration system (Amicon DC 10) using hollow fiber columns (DIAFLO, HIX 50-8 and HIP 100–200) having a diameter of 2.3 cm and length of 20.3 cm at an inlet pressure of about 10 to 50 PSI and operating temperature of about 20° to 60° C. This first dialysis procedure removed the aloe vera gel's components of less than about 10,000 molecular weight. The non-dialyzable fraction I which included the gel components having a molecular weight greater than about 10,000 was then dialyzed a second time in a hollow fiber column against distilled water for about twenty four (24) hours. This second dialysis removed components of less than about 30,000 molecular weight. The non-dialyzable fraction II resulting from the second dialysis was lyophilized and produced two bands when subjected to gel electrophorisis using polyacrylamide gel, indicating the presence of two major components. The non-dialyzable fraction II was then dialyzed for a third time in a hollow fiber column against distilled water for about 24 hours thereby removing components with a molecular weight less than about 70,000 producing a substantially pure, non-dialyzable fraction III. The non-dialyzable fraction III was then concentrated and lyophilized producing 0.18 grams of the aloe isolate of this invention which produces a single band in gel electrophorsis using polyacrylamide gel. A freeze dried portion of the aloe isolate showed a symmetrical, geometric lattice-like drying pattern. A high pressure liquid chromatogram (FIG. 3) of the aloe isolate produced a single peak indicating that only a single compound was present. Quantitative analysis of the aloe isolate indicated that it was approximately 95% by wt. polysaccharide having the elemental analysis given above at page 4 from which the following emperical formula was deduced $(C_{322}, H_{620}, N, S_3, O_{336} P)_7$.

Samples of the aloe isolate were hydrolized in 6N hydrochloric acid at 110° C. for 24 hours and the resulting hydrozylates were qualitatively determined by paper and gas chromatography, which indicated the presence of mannose, glucose, arabinose, rhamnose and galactose. The aloe isolate also tested positive for carbohydrates and negative for protein by the ninhydrin test.

Comparison of Aloe Vera Gel and Aloe Isolate Cell Growth Ability

Fibroblast skin cells were obtained in a frozen ampule which was thawed in a waterbath at 37° C. with shaking. The ampule was then transferred into a beaker containing 70% ethanol and opened under asceptic conditions and its content transferred to a culture flask. The resultant cell suspension was diluted with an appropriate volume of culture medium (Dulbecco's Modified Eagle) and incubated at 37° C. to allow the cells to attach to and proliferate on the glass surface. Approximately 300,000 cells were inoculated.

Stock solutions of the aloe vera gel and the aloe isolate were prepared and diluted with the medium to obtain the desired concentrations. Sterile techniques were used throughout the experimental study. The culture medium was decanted from the culture bottles containing the skin fibroblast cells and the cells were washed once with a maintenance medium. Previously prepared serial dilutions of each of the test agents were dispensed into a sufficient number of bottles of cells to provide two bottles of each dilution of the test agents for test periods of 24, 48 and 72 hours. At the same time, sufficient bottles of cells were inoculated with maintenance medium to provide two control bottles for each experimental period.

At the end of 24, 48 and 72 hours, two bottles of each dilution and two control bottles were trypsinized with 3.0 ml of 0.25% trypsin solution to remove the cells from the surfaces of the bottles. After treatment with Trypsin for 15 minutes, the Trypsin solution containing the cells was pipetted into 15 ml screw-cap tubes and centrifuged for 5 minutes. The liquid was decanted from the cells, and the cells were resuspended in medium and again centrifuged for 5 minutes, 0.3 ml of 0.5% Trypan blue stain was then added to the suspension of cells in the maintenance medium. After the cells were exposed to this stain for 3 minutes, they were re-suspended by aspiration with a pipette. Aliquots were placed in the counting chamber of Hemacytometer, and the cells were counted. The number of cells in six aliquots from each bottle was counted and the total number of viable cells was determined. The non-viable cells were stained blue while the viable cells remained unstained and appeared colorless. It can be seen from the data presented in FIG. 4 that the aloe isolate of this invention is far superior to aloe vera gel in enhancing cell growth.

Preliminary experiments were also conducted to determine the relative toxicity of each of the test agents to the cells. Cells growing in glass prescription bottles were exposed to various dilutions of the test agent solutions for time intervals of up to 72 hours to determine the highest concentration of the test solutions that could be used without causing complete cell destruction. Preliminary qualitative observations revealed that the 0.1% dilution of the gel was relatively toxic during early time periods and completely toxic at the end of 72 hours.

It has also been discovered that the aloe isolate of this invention and aloe vera gel itself act as antidotes to certain poisons, i.e., curare and atropine. Mice injected with about 10 to 25 mg per kg body weight of the aloe isolate of this invention showed better survival rate than control mice when poisoned.

What is claimed is:

1. A substantially pure pharmaceutically active aloe isolate comprising:

a polysaccharide including nitrogen, sulfur and phosphorous and having a molecular weight of about 70,000;

having an infra red spectra with principal peaks at about 3400, 2900, 1720, 1550 and 1420 cm$^{-1}$; and an NMR spectrum with absorbtion peaks at about 20 ppm (singlet) 70 ppm (broad multiplet) and 174 ppm (broad multiplet).

2. The substantially pure pharmaceutically active aloe isolate according to claim 1, wherein the polysaccharide has the following elemental analysis C, 38.60%; H, 6.20%; O, 53.80%; S, 1.04%; N, 0.13% and P, 0.13%.

3. The substantially pure pharmaceutically active aloe isolate according to claim 1 derived from an aloe plant selected from the group consisting of *aloe vera linne* and *aloe barbadensis*.

4. A method for preparing a substantially pure aloe isolate, comprising the steps of:

(A) separating aloe gel from an aloe plant;

(B) dialyzing the gel against water; and (C) repeating step B to produce an aloe isolate comprising a polysaccharide including nitrogen, sulfur and phosphorous and having a molecular weight of about 70,000;

having an infra red spectra with principal peaks at about 3400, 2900, 1720, 1550 and 1420 cm$^{-1}$; and an NMR specturm with absorbtion peaks at about 20 ppm (singlet), 70 ppm (broad multiplet) and 174 ppm (broad multiplet).

5. The method according to claim 6 wherein the aloe plant selected from the group consisting of *aloe vera linne* and *aloe barbadensis*.

* * * * *

UNITED STATES PATENT AND TRADEMARK OFFICE
CERTIFICATE OF CORRECTION

PATENT NO. : 4,861,761

DATED : August 29, 1989

INVENTOR(S) : Valdemar H. Madis et al.

It is certified that error appears in the above-identified patent and that said Letters Patent is hereby corrected as shown below:

Column 5, line 24, change "toxic" to --nontoxic--.

Signed and Sealed this

Fifth Day of November, 1991

*Attest:*

HARRY F. MANBECK, JR.

*Attesting Officer*      *Commissioner of Patents and Trademarks*